(12) United States Patent
Ehret et al.

(10) Patent No.: US 6,224,874 B1
(45) Date of Patent: May 1, 2001

(54) PROCESS FOR THE PRODUCTION OF IRONES

(76) Inventors: Charles Ehret, 65 Usterstrasse, CH-8620 Wetzikon (CH); Laurence Marthe Marie Firmin, 23, Rue Joseph Malleville, F-76290 Fontaine-la-Mallet; Didier Courtois, 87 bis Rue de Coulmiers, F-45000 Orléans, both of (FR)

( * ) Notice: Subject to any disclaimer, the term of this patent is extended or adjusted under 35 U.S.C. 154(b) by 0 days.

(21) Appl. No.: 09/202,905
(22) PCT Filed: Apr. 23, 1998
(86) PCT No.: PCT/EP98/02407
    § 371 Date: Jun. 28, 1999
    § 102(e) Date: Jun. 28, 1999
(87) PCT Pub. No.: WO98/49139
    PCT Pub. Date: Nov. 5, 1998

(30) Foreign Application Priority Data

Apr. 30, 1997 (EP) .................................................. 97107175

(51) Int. Cl.⁷ .................................................. A01N 65/00
(52) U.S. Cl. .......................................................... 424/195.1
(58) Field of Search .......................................... 424/195.1

(56) References Cited

U.S. PATENT DOCUMENTS 4,963,480  10/1990  Belcour et al. .
5,085,994   2/1992  Baccou et al. .
5,106,737   4/1992  Gil et al. .

FOREIGN PATENT DOCUMENTS 0 353 683  2/1990  (EP) .
0 443 925  8/1991  (EP) .
2 620 702  3/1989  (FR) .
2 653 637  5/1991  (FR) .
  293843   1/1971  (SU) .

OTHER PUBLICATIONS

Krick, W., et al., "Isolation and Structure Determination of the Precursors of α– and γ–Irone and Homologous Compounds from *Iris florentina*," *Naturforsch*, 38C, pp. 179–184 (1983).

Jehan, H., et al., "Selection clonale d'iris à parfum." *C.R. Acad. Sci. Paris, Sciences de la vie/Life Sciences*, 317: pp. 424–429 (1944).

Chem Abstracts, vol. 75, No. 10, No. 67385w (1971).

Derwent English language abstract of SU 293843.

Derwent English language abstract of FR 2620702.

*Primary Examiner*—Sandra Saucier
(74) *Attorney, Agent, or Firm*—Mark E. Waddell; Stephen M. Haracz; Bryan Cave LLP

(57) ABSTRACT

A process for the preparation of irones by a chemical oxidation of irone precursors, comprising treating an iris rhizome substrate selected from the group consisting of iris rhizomes, parts of such rhizomes, iris extracts, iris extraction wastes, any plant tissues containing precursors of irones and mixtures thereof, is described.

17 Claims, No Drawings

PROCESS FOR THE PRODUCTION OF IRONES

BACKGROUND OF THE INVENTION

Today, irone extracts are produced by solvent extraction or steam distillation of the rhizomes of any iris species, preferably *Iris pallida* or *Iris germanica*. After a cultivation period of 2–3 years the rhizomes are harvested and stored for 3–5 years at room temperature. During this maturation period the irones are released from their precursors (W. Krick, F. J. Marner, and L. Jaenicke, Z. Naturforsch. 1983, 38c 179–184). Then the irones are recovered by steam distillation (as iris butter) or solvent extraction (leading to a resinoid) of the powdered rhizomes leading to valuable iris materials for the flavour and fragrance industry.

This long period of maturation is cumbersome, expensive, needs extensive storage capacity and leads to the loss of part of the isomers in uncontrolled degradation reactions.

Several alternatives to this non-effective and time consuming maturation period have been proposed. In a first proposal (FR-2 620 702, 24/3/89) by Buono et al., a lipohilic extract of the iris rhizomes containing the irone precursors is oxidized with $KMnO_4$ in an organic solvent; in this procedure the extraction of the precursors is laborious and due to this unusual downstream processing (working-up), namely the extraction of the precursors before the oxidation, the quality of the resulting product is quite different from the traditionally preferred Iris Butter or Absolute. A reduction of the maturation period to two months has been disclosed in FR-2 653 637, 3/5/91, by Baccou et al., with a preliminary treatment of the fresh, i.e. not maturated iris rhizomes with ionizing radiation; but the claimed yields hardly reach the irone contents (<400 mg/kg dry rhizomes) obtained during maturation by a 2–3 years period of storage. Bioconversions of lipophilic extracts of the rhizomes with fungi of the genus Botryonia (EP 0 443 925; 23/8/91) by Gil et al. or with peroxidizing enzymes (EP 0 443 926; 28/8/91) by Gil et al., have been disclosed; they lead to a good conversion of the precursors but again present the disadvantage of the preliminary solvent extraction and consequently lead to a product whose quality differs from the preferred iris butter. The bioconversion of powdered iris rhizomes by bacteria of the family Enterobacteriacea in the presence of a plant cell medium (EP 0 353 683, U.S. Pat. No. 4,963,480) by Belcour et al., releases the irones from their precursors, and, after steam distillation produces an iris butter of excellent quality characterized by a high content of irones. A drawback is that the long maturation period has been replaced by a rather expensive microbiological treatment.

SUMMARY OF THE INVENTION

The present invention relates to a new process for the preparation of irones. In particular the invention relates to the treatment of iris rhizomes, parts of such rhizomes, iris extracts, plant tissues or any source of irone precursors, with nitrite salts in order to release, i.e. to form, to produce the irones.

Under irones there is to be understood a mixture of the isomers gamma-irone, cis-alpha-irone, trans-alpha-irone and beta-irone as usually found in extracts of iris species.

Under irone precursors there are to be understood compounds or any mixture of such compounds which, when treated with the nitrite, lead to irones. The use of selected clones of iris species characterized by a high content of irone precursors is preferred.

One embodiment of the invention is a process for the preparation of irones, which process includes treating iris rhizomes, parts of such rhizomes, iris extracts, iris extraction wastes, or any iris plant tissue containing precursors of irones and mixtures thereof, with an aqueous solution of a nitrite, and recovering the irones formed therefrom.

DETAILED DESCRIPTION OF THE INVENTION

Surprisingly it has now been found that the treatment, e.g. at mild temperatures, of rhizomes, e.g. powdered fresh iris rhizomes with an aqueous solution of a nitrite salt liberates, i.e. forms the irones, under mild conditions and with excellent yields. The isomeric and enantiomeric distribution of the resulting irones is identical to that obtained after a traditional maturation.

Various cations may be associated to the nitrite anion. Good results were obtained with alkali metal, alkaline earth or ammonium nitrites, e.g. with sodium nitrite, potassium nitrite, calcium nitrite, ammonium nitrite, etc. preferably sodium or potassium nitrite.

A suitable concentration of nitrite salts is from about 0.1 g/L to about 5 g/L, and, preferably from about 0.5 to about 1 g/L.

A suitable range of the ratio by weight of iris rhizome substrate to medium, i.e. the aqueous solution, is from about 1:20 to about 2:1, with about 1:5 to about 1:20 being preferred.

A suitable pH range for the treatment with aqueous nitrite solutions is from 1 to about 6, more preferably from about 2 to about 5. The preferred pH is between about 2 and about 3.

Any suitable acid, e.g. $H_3PO_4$, or other mineral acids may be used to adjust the desired pH value.

The treatment is effective at mild temperatures. Best results are obtained between ca. 10 and ca. 50° C. and preferably at ambient temperatures, e.g. between 20 and 30° C.

The time necessary to complete the generation of the irones is dependant upon the conditions of the treatment. A suitable reaction time for the process is from about 1 hour to about 5 days, with about 5 to about 36 hours being preferred.

Table 1 shows the results of a kinetic study of the production of irones by treatment of iris rhizomes with a solution of sodium nitrate at ambient temperature.

In the example, the treatment of freshly harvested rhizomes of *Iris pallida* with an initial irone content of 12 mg/kg dry rhizomes, in suspension at 100 g/L in a 0.1% solution of sodium nitrite at pH 2.5 and at a temperature of 25° C. liberates between 1200–1400 mg irones/kg dry rhizomes after 30 hours.

Rhizomes of the genera Iris (Iridacea family), parts of such rhizomes, iris wastes or extracts and more generally all plant tissues containing precursors of irones can be used. The substrate of the present invention is preferably obtained from an iris plant selected from the group consisting of *I. pallida, I. germanica, I. florentina*, preferably *I. pallida*.

The iris substrate, which is preferably taken from the plant in a vegetative, i.e. growing state, may be used fresh or shortly after harvest, e.g. in the form of:

iris rhizomes, e.g. crushed or powdered,
  iris rhizome parts, iris rhizome extracts, e. g., extracts using any organic solvent dissolving the irone precursors, preferably alcoholic e.g. alkanolic, and preferably methanolic extracts,
  iris wastes, i.e. the residues recovered after the industrial extraction of iris rhizomes, plant cell cultures of iris, initiated as described, e.g. in EP 0 353 683 or mixtures thereof.

The extraction of the final product is conveniently carried out by conventional methods as used nowadays for the isolation of volatiles from plants, e.g. for the production of fragrances and flavours raw materials, i.e., hydrodistillation (steam distillation), extraction using any suitable volatile organic solvent, i.e alcohols, hexane, and mixtures thereof. By the preferred method, i. e. hydrodistillation, the resulting iris butter contains, e.g. 15–30% of irones depending on the quality of the rhizomes.

It has surprisingly been found that among a collection of different clones of Iris, e.g. of *Iris pallida* and *Iris germanica*, of various origins, an important variability was observed as far as the content of irone precursors is concerned (Jehan et al., C.R. Acad. Sci. Paris, Sciences de la vie/Life science, 1994; 317: 424–429). Thus applying the above described maturation process on 56 different plants (*I. pallida*), the irone content after treatment has been shown to be within the range of ca.1100–ca.1800 mg irones/kg dry rhizomes. Several clones have been found which exceed the irone content of an average population of commercial *I. pallida* rhizomes by a factor of over 50% to 65%. Thus the present invention relates also to the use of the new maturation process to such selected clones, e.g. the clones GRN1, GRN2, characterized by a high irone precursor content for the production iris extracts.

This method is thus based on a pure selection work in the field from an established collection of, e.g. 56 clones, of *Iris pallida*. The evaluation of the irone content is effected by microbiological treatment as described by Jehan et al. Multiplication, micropropagation and cultivation are effected as known in the art.

The present invention is further illustrated by the following examples which are not intented to limit the effective scope of the claims.

EXAMPLES

Example 1
Production of Irones by Treatment of Rhizomes of *Iris pallida*

Fresh rhizomes are first cleared from excess earth and ground in a Warring Blender.

To a solution of 5 g of sodium nitrite in 5 liters of water, ground fresh iris rhizomes (*Iris pallida*, 500 g, initial irone content: 12 mg irones/kg dry rhizomes) are charged in a reaction vessel equiped with a mechanical stirrer. After the pH has been adjusted to 2.5 with 5 molar $H_3PO_4$, the mixture is gently stirred at room temperature for 48 hours.

[For the determination of the irone content in the reaction mixture after the "maturation", 50 ml of the reaction mixture are mixed with 20 ml of 1 molar sodium hydroxyde solution and extracted with a 80/20 v/v mixture of MTBE (methyl-t-butyl ether) and ethanol in the presence of an internal standard (anethole). After centrifugation the organic layer is analyzed by GC (Carbowax 20M column, 30 m, diameter 0.32 mm, program 60° C. 4 min, 12° C./min until 150° C., 3° C./min until 240° C.). The maturated suspension contains 1840 mg irones/kg dry rhizomes.]

The resulting maturated mixture is hydrodistilled in a distillation apparatus equipped with a short path column, a condenser (phase separator) for the total distillate and a set-up for recycling of the aqueous phase. The resulting Iris butter (1.85 g, yield 0.37%/fresh rhizomes or 0.92%/dry rhizomes) is recovered at the surface of the receptor vessel.

The Iris butter is analyzed by GC in the presence of an internal standard: ca. 50 mg of Iris butter are exactly weighed into a 50 ml flask; after addition of the internal standard and 5 ml of 1 molar sodium hydroxyde solution, the heterogeneous mixture is stirred vigourously during 15 minutes; 5 ml of the resulting upper phase are mixed with 1 ml of methanol and analyzed by GC as described above. The resulting Iris butter has an irone content of 16.2%.

Example 2
Production of Irones by Treatment of Rhizomes of *Iris pallida* Selected for their High Irone Precursor Content For these experiments, 2 types of *Iris pallida* rhizomes have been used:

Batch I: Fresh rhizomes from 56 different plants (3 years old) in a vegetative state are first cleared from excess earth. Three aliquots of each plant sample (3×5 g) are cut into small pieces and ground in a Warring Blender. Then the rhizomes are put in Erlenmeyer flasks (8 g in 50 ml of aqueous $NaNO_2$ 1g/liter at pH 2.5 in each flask). The 3 flasks are placed on a gyratory shaker (100 revolutions/minute) at 25° C. during 24 hours. A control experiment is performed following the same procedure without the $NaNO_2$ solution.

At the end of the 24 hours period, both the rhizomes and the aqueous phase are extracted with MTBE, together or separately, (i.e. by separating the rhizome parts by filtration or centrifugation). The combined extracts (extracted rhizomes and aqueous phase), are analyzed by gas chromatography (GC) as described in example 1.

Batch II: Two clones (GRN1 and GRN2) which previously had been selected for their growth and high content in irone precursors by the technique described in "C.R. Acad. Sci. Paris, Sciences de la vie/Life science, (317) 424–429 (1994)", from the 56 clones of various origins after 3 years of cultivation. The fresh rhizomes were treated as above (Batch I)

The results (expressed in mg of irones/kg of dry-weighed iris rhizome) are shown in Table 1. Standard deviations correspond to 3 replications in fields.

As currently demonstrated, the control sample (fresh harvested rhizome without any treatment) contains very few quantities of irones (less than 100 mg/kg dry weight).

TABLE 1

|  | Batch I(*) | Batch II (GRN1) | Batch II (GRN2) |
| --- | --- | --- | --- |
| Treatment with $NaNO_2$ | 1339 (+−208) (*) mean of 56 clones of *Iris pallida* of various origins | 1716 (+−115) | 1659 (+−134) |

Example 3
Production of Irones by the Treatment of an *Iris pallida* Rhizome Extract A crude extract of iris rhizomes (Batch I, see example 1) is obtained of 50g of fresh material ground in a Warring Blendor, then follows an extraction with 3 times 250ml $CHCl_3$/MeOH (1/2) under agitation during 1 hour. After filtration, the combined fractions are concentrated. The resulting crude extract is dissolved in 10 ml of MeOH. The solution is added to a $NANO_2$ solution (500 ml, 1 g/liter) at pH 2.5, 25° C., and stirred (100 rpm) during 24 hours. The total solution is extracted and analyzed as described in Example 1. An aliquot of fresh rhizomes (before extraction) is treated as in Example 1. The results (expressed in mg of irones/kg of dry-weighed iris rhizome) are listed in Table 2

TABLE 2

|  | Fresh rhizomes (before extraction) | extract |
|---|---|---|
| Treatment with NaNO$_2$ | 1025 (+−130) | 1266 (+−25) |

What is claimed is:

1. A process for the preparation of irones, comprising treating iris rhizomes, parts of such rhizomes, iris extracts, iris extraction wastes, or any iris plant tissue containing precursors of irones and mixtures thereof, with an aqueous solution of a nitrite, and recovering the irones formed.

2. The process according to claim 1 wherein the iris rhizomes are selected from the group consisting of *Iris pallida, Iris germanica, Iris florentina*, Iris of Verona, and mixtures thereof.

3. The process according to claim 1 wherein an aqueous solution of an alkali, alkaline earth or ammonium nitrite is used.

4. The process according to claim 3 wherein the aqueous solution is sodium nitrite.

5. The process according to claim 1 wherein the iris rhizomes are fresh and non-matured.

6. The process according to claim 1 wherein the iris rhizomes are in the form of an iris rhizome extract.

7. The process according to claim 1 wherein the iris rhizomes are in the form of an iris rhizome extraction waste.

8. The process according to claim 1 wherein the iris rhizomes are in the form of a plant cell culture of iris.

9. The process according to claim 1 wherein the irones recovered are selected from the group consisting of gamma-irone, cis-alpha-irone, trans-alpha-irone, beta-irone, and mixtures thereof.

10. The process according to claim 1 wherein the process is carried out between about 20° C. and about 30° C.

11. The process according to claim 1 wherein the process is carried out for a period of about 1 to about 120 hours.

12. The process according to claim 11 wherein the process is carried out for about 5 hours to about 36 hours.

13. The process according to claim 1 wherein the concentration of the nitrite salt is 0.1 to about 5 g/liter of the reaction medium.

14. The process according to claim 1 wherein the process is carried out in a pH range of about 1 to about 6.

15. The process according to claim 14 wherein the process is carried out in a pH range of between about 2 to about 5.

16. The process according to claim 1 wherein the range of iris rhizomes to aqueous solution is from about 1:20 to about 2:1 (weight/weight).

17. The process according to claim 1 wherein the irones are recovered by extraction or distillation.

* * * * *